(12) United States Patent
Oftring et al.

(10) Patent No.: US 7,915,454 B2
(45) Date of Patent: Mar. 29, 2011

(54) METHOD FOR PRODUCING ETHYLENEDIAMINE

(75) Inventors: Alfred Oftring, Bad Dürkheim (DE); Kirsten Dahmen, Freinsheim (DE); Randolf Hugo, Dirmstein (DE); Thilo Hahn, Kirchheimbolanden (DE); Katrin Baumann, Mannheim (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 26 days.

(21) Appl. No.: 12/529,107

(22) PCT Filed: Feb. 28, 2008

(86) PCT No.: PCT/EP2008/052435
§ 371 (c)(1), (2), (4) Date: Aug. 28, 2009

(87) PCT Pub. No.: WO2008/104592
PCT Pub. Date: Sep. 4, 2008

(65) Prior Publication Data
US 2010/0094057 A1   Apr. 15, 2010

(30) Foreign Application Priority Data

Mar. 1, 2007  (EP) .................................... 07103290

(51) Int. Cl.
*C07C 209/48*  (2006.01)
(52) U.S. Cl. ...................................... 564/490; 564/492
(58) Field of Classification Search .................. 564/490, 564/492
See application file for complete search history.

(56) References Cited

U.S. PATENT DOCUMENTS

| | | | |
|---|---|---|---|
| 2,429,876 A | 10/1947 | Gresham | |
| 2,519,803 A | 8/1950 | Weber et al. | |
| 3,255,248 A | 6/1966 | Suessenguth et al. | |
| 3,478,102 A * | 11/1969 | Hansel et al. | 564/492 |
| 3,574,754 A * | 4/1971 | Specken | 564/493 |
| 3,972,940 A | 8/1976 | Morgan, Jr. | |
| 4,235,821 A | 11/1980 | Butte, Jr. et al. | |
| 5,530,127 A | 6/1996 | Reif et al. | |
| 6,297,394 B1 | 10/2001 | Voit et al. | |
| 6,469,211 B2 | 10/2002 | Ansmann et al. | |
| 6,852,669 B2 | 2/2005 | Voit et al. | |
| 7,091,153 B2 | 8/2006 | Voit et al. | |

FOREIGN PATENT DOCUMENTS

| | | |
|---|---|---|
| DE | 1154121 | 9/1963 |
| DE | 3003729 A1 | 8/1980 |
| EP | 0382508 A2 | 8/1990 |
| EP | 0696572 A1 | 2/1996 |
| EP | 0963975 A1 | 12/1999 |
| EP | 1209146 B1 | 6/2004 |
| EP | 1742045 A1 | 1/2007 |
| WO | WO-9944984 A1 | 9/1999 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,101, filed Aug. 28, 2009.
U.S. Appl. No. 12/529,096, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,079, filed Aug. 28, 2009.
U.S. Appl. No. 12/529,087, filed Aug. 28, 2009.

* cited by examiner

*Primary Examiner* — Brian J Davis
(74) *Attorney, Agent, or Firm* — Connolly Bove Lodge & Hutz LLP

(57) ABSTRACT

The invention relates to a process for preparing ethylenediamine by hydrogenation of aminoacetonitrile over a catalyst, wherein the hydrogenation is carried out in a solution comprising aminoacetonitrile, water in a proportion of from 0 to 60% by weight and a solvent and the aminoacetonitrile comprised in the solution is fed into the reaction vessel at a rate which is not greater than the rate at which the aminoacetonitrile reacts with hydrogen in the hydrogenation.

19 Claims, No Drawings

METHOD FOR PRODUCING ETHYLENEDIAMINE

CROSS-REFERENCE TO RELATED APPLICATIONS

This application is a national stage application (under 35 U.S.C. §371) of PCT/EP2008/052435, filed Feb. 28, 2008, which claims benefit of European application 07103290.8, filed Mar. 1, 2007.

BACKGROUND OF THE INVENTION

The invention relates to a process for preparing ethylenediamine by hydrogenation of aminoacetonitrile over a catalyst.

Ethylenediamine (EDA) can be prepared by hydrogenation of aminoacetonitrile (AAN) and is a starting material for, for example, the synthesis of complexing agents or bleaching activators which are used, inter alia, as additives for laundry detergents or cleaners.

It is generally known that nitriles can be hydrogenated in the presence of catalysts to give the corresponding amines. Depending on the reaction parameters selected, the known processes give the desired products, for example primary amines as main product and secondary and tertiary amines as by-products. A problem here is often that the desired product is obtained with lower selectivity and/or in lower yield, frequently also accompanied by rapid deactivation of the catalyst used.

Numerous processes for hydrogenating the α-amino nitriles aminoacetonitrile (AAN) and iminodiacetonitrile (IDAN) or β-amino nitriles have been described in the prior art. Thus, it is known that the hydrogenation of β-amino nitriles generally proceeds without problems, while the hydrogenation of α-amino nitriles is associated with the occurrence of numerous disadvantages such as hydrogenolysis of the C—CN bond or the $R_2N$—C bond, "Handbook of Heterogeneous Catalytic Hydrogenation for Organic Synthesis, pp. 213 to 215" indicates the problems of the hydrogenation of α-amino nitriles for the example of α-alkylamino nitriles or cyclic α-aminonitriles compared to β-amino nitriles. The known stability problems of α-amino nitriles are presumably the reason why to the present day only the hydrogenation of the α-amino nitriles AAN or IDAN to EDA (ethylenediamine) or DETA (diethylenetriamine), respectively, has been described in detail. However, a corresponding hydrogenation is not known for higher α-amino nitriles.

The stability of AAN also differs significantly from the stability of IDAN, as can be shown by dynamic differential calorimetry. While the onset is at 220° C. in the case of IDAN, in the case of AAN decomposition is observed at a temperature as low as 150° C.

In processes for preparing amines by hydrogenation of nitriles, it is also known that a certain amount of ammonia favors the selectivity of the hydrogenation to primary amines and suppresses the formation of secondary and tertiary amines. However, the hydrogenation in the presence of ammonia involves an additional engineering outlay associated with separation from the product stream, work-up and possible recirculation of the ammonia. In addition, relatively high pressures can be necessary in the hydrogenation, since the partial pressure of the ammonia has to be taken into account.

DE-A 3 003 729 describes a process for hydrogenating aliphatic nitriles, alkylene oxy nitriles and alkylene amino nitriles to primary amines over a cobalt or ruthenium catalyst in the presence of a solvent system. The solvent system used comprises water and ammonia together with an ether or polyether which preferably has from 4 to 6 carbon atoms and a hydrocarbon to oxygen ratio of from 2:1 to 5:1, e.g. dioxane, tetrahydrofuran, methylene glycol dimethyl ether or diethylene glycol dimethyl ether, with cyclic ethers such as dioxane and tetrahydrofuran being particularly preferred. As nitrile component, dinitriles are particularly preferred. On the other hand, DE-A 3003 729 does not disclose that compounds which have both a cyano group and an amino group, e.g. such as AAN, can be used in this process.

EP-A 0 382 508 describes a process for the batchwise preparation of acyclic, aliphatic polyamines by hydrogenation of acyclic, aliphatic polynitriles in the liquid phase over Raney cobalt catalysts, for example in the presence of anhydrous ammonia. Here, a polynitrile solution is fed into a reaction zone which comprises the Raney cobalt catalyst in an essentially oxygen-free atmosphere. During the entire time of the reaction, the polynitrile solution is fed in at a rate which is no greater than the maximum rate at which the polynitrile reacts with the hydrogen in the reaction zone. Furthermore, mention is made of a reaction parameter K which is suitable for determining the volumetric feed rate. The process described is restricted to the preparation of polyamines from polynitriles such as iminodiacetonitrile (IDAN), nitrilotriacetonitrile or compounds having more than 2 cyano groups. However, the reaction of compounds having one cyano groups, e.g. AAN to EDA, is not described.

U.S. Pat. No. 3,972,940 relates to a method of preventing foaming of the suspension of a Raney nickel or Raney cobalt catalyst used in the catalytic hydrogenation of nitriles to the corresponding amines. In this method, both the appropriate nitrile and the catalyst suspension are fed continuously into the reaction zone. In the reaction zone, the nitrile used is hydrogenated to the corresponding amine and unreacted nitrile, the catalyst and the amine, in particular hexamethylenediamine, are removed from the reaction zone. Foaming of the catalyst suspension is suppressed by a partial amount of the amine (product) discharged from the reaction zone being introduced into the catalyst suspension before the catalyst suspension is fed into the reaction zone. However, U.S. Pat. No. 3,972,940 gives no information about the rate or amount at which/in which the nitrile used is fed into the reaction zone. Furthermore, neither AAN nor EDA are explicitly mentioned in this document.

U.S. Pat. No. 2,519,803 describes a process for preparing ethylenediamine by hydrogenation of a partially purified aqueous reaction mixture which results from amination of formaldehyde cyanohydrin and comprises aminoacetonitrile as intermediate. The partially purified aqueous reaction mixture is cooled to about 5° C. for a maximum of 30 minutes before it is passed to the hydrogenation. The hydrogenation preferably takes place in the presence of $NH_3$.

DE-A 1 154 121 relates to a further process for preparing ethylenediamine, in which the starting materials hydrocyanic acid, formaldehyde, ammonia and hydrogen are reacted in the presence of a catalyst in a one-pot process. Both the ammonia and the hydrogen are used in a molar excess over the further starting materials hydrocyanic acid and formaldehyde which are present in equimolar amounts. In this process, the AAN formed in situ is thus not isolated but directly reacted further with hydrogen. A disadvantage of this process is that the desired product (EDA) is obtained relatively unselectively in small amounts.

U.S. Pat. No. 3,255,248 describes a process for the hydrogenation of organic nitrogen-carbon compounds which preferably have amino groups substituted by nitro, N-nitroso, isointroso, cyano or aromatics to the corresponding amines in the liquid phase using a sintered catalyst comprising cobalt or nickel. Here, the starting material is trickled, either alone or in the presence of a solvent such as water, tetrahydrofuran, methanol, ammonia or the reaction product formed, together with the hydrogen onto the catalyst. If unsaturated compounds such as cyano groups are hydrogenated on the nitrogen atom, the presence of ammonia in the reaction is recommended. This is made clear in example 1 of this patent, where aminoacetonitrile in the form of an aqueous solution is trickled down with liquid ammonia but without the solvent onto the sintered catalyst. However, U.S. Pat. No. 3,255,248 gives no information about the rate at which the starting material is fed in.

EP-A 1 209 146 relates to a further process for the continuous hydrogenation of nitriles to primary amines, in which the respective nitriles are reacted in the liquid phase over a suspended, activated Raney catalyst based on an aluminum alloy and the reaction is carried out in the absence of ammonia and basic alkali metal or alkaline earth metal compounds. Among many other nitriles, AAN and IDAN can be reacted to give the corresponding ethylene amines. If appropriate, the nitrile to be hydrogenated can also be present in dissolved form in an organic solvent, with preference being given to using alcohols, amines, amides, in particular N-methylpyrrolidone (NMP) and dimethylformamide (DMF) and also ethers or esters as solvents. However, EP-A 1 209 146 gives no information about the rate at which the respective nitrile is fed into the reaction vessel (reactor).

BRIEF SUMMARY OF THE INVENTION

It is therefore an object of the present invention to provide a simple, inexpensive and variable process for preparing ethylenediamine by hydrogenation of aminoacetonitrile, which gives ethylenediamine at a high conversion and/or with high selectivity.

This object is achieved by a process for preparing ethylenediamine by hydrogenation of aminoacetonitrile over a catalyst, wherein the hydrogenation is carried out in a solution comprising aminoacetonitrile, water in a proportion of from 0 to 60% by weight (based on the aminonitrile/water mixture) and a solvent and the aminoacetonitrile comprised in the solution is fed into the reaction vessel at a rate which is not greater than the rate at which the aminoacetonitrile reacts with hydrogen in the hydrogenation.

DETAILED DESCRIPTION OF THE INVENTION

The process of the invention has the advantage that ethylenediamine can be prepared at a high conversion and/or with high selectivity. The starting material used (AAN) is preferably reacted completely or virtually completely. This is particularly important in industrial processes since unreacted starting material generally has to be recirculated to the process circuit or be disposed of. Processes in which large amounts of AAN are not reacted are particularly disadvantageous because of the high instability of AAN. Firstly, AAN tends to decompose at relatively high temperatures, so that the decomposition products cannot be recirculated to the circuit, and secondly this decomposition can also proceed with explosive vigor. Since the AAN can be reacted completely in the process of the invention, no efforts have to be made to recirculate it to the production cycle.

The object of the process of the invention is that the catalyst used has a longer life (lower catalyst consumption) and that the space velocity over the catalyst is also higher than in comparable processes. Owing to the higher space velocity over the catalyst, a higher space-time yield of product (EDA) can be achieved.

The process of the invention starts out from the starting material aminoacetonitrile (AAN), with it generally being possible to use any type of AAN. Preference is given to using distilled AAN. It is also conceivable to carry out the process of the invention directly subsequent to the AAN synthesis, with AAN preferably being prepared by reaction of formaldehyde cyanohydrin (FACH) and ammonia by methods known to those skilled in the art. Preference is given to using AAN which is largely free of FACH (FACH-free). For the purposes of the present invention, FACH-free means that not more than 1 mol % of FACH is present in the AAN used, based on the amount of AAN. The AAN is preferably completely free of FACH. A correspondingly low FACH content in the AAN can be achieved, for example, by means of a sufficiently long starting material residence time and/or a reaction temperature which is not too low in the reaction of $NH_3$ and FACH. The AAN is mixed with a solvent and possibly with water and the solution obtained is used in the process of the invention. The use of a solvent is found to be advantageous since stabilization of AAN is achieved and introduction at a desired rate into the apparatus for carrying out the process can be simplified. In addition, a rinsing effect on the catalyst used can be achieved, as a result of which its operating life is increased (longer catalyst life) and the space velocity over the catalyst is improved.

A suitable solvent which can comprise one or more components should have the following properties:

(a) the solvent should have a stabilizing effect on AAN, in particular suppress decomposition of AAN at the prevailing temperatures;
(b) the solvent should have a good dissolution capability for hydrogen;
(c) the solvent should be inert and from a single phase under the reaction conditions;
(d) in a preferred separation of the product from the product stream by distillation after the hydrogenation, the solvent should form no azeotropes with the product or products;
(e) the solvent should have an appropriately low boiling point.

Possible solvents are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as ethylene amines, alkylamines, esters such as methyl acetate or ethyl acetate and ethers such as diisopropyl ether, diisobutyl ether, glycol dimethyl ether, diglycol dimethyl ether, dioxane and tetrahydrofuran (THF). Ethers are preferably used in the process of the invention, more preferably cyclic ethers and particularly preferably tetrahydrofuran. In a further preferred embodiment, alcohols, in particular methanol, are used as organic solvent.

The solvent is used in a weight ratio to the amino nitrile mixture used of from 0.1:1 to 15:1. The concentration of the amino nitrile mixture in the solution in which the hydrogenation is carried out should be selected so that a suitable feed rate or residence time can be set. Preference is given to mixing aminoacetonitrile in an amount of from 10 to 90% by weight with the solvent. Based on the particularly preferred solvents methanol and tetrahydrofuran, it is advantageous, for example, to use the amino nitrile mixture in an amount of from 20 to 50% by weight based on the solvent.

The solution used for the preparation of ethylene amines by hydrogenation of the amino nitrile mixture can comprise a proportion of water in addition to the amino nitrile mixture and any solvent. if water is present, the proportion by weight of water in the solution is in the range from 0 to 70%, preferably from 10 to 50%. The amounts of water indicated are based on the amino nitrile/water mixture.

If appropriate, additional additives can be comprised in the solution in which the hydrogenation is carried out. Possible additives are principally hydroxides such as alkali metal hydroxides, alkoxides, amides or ammonia. Furthermore, acidic additives such as silicates can be additionally comprised in the solution. These substances can be added as pure substance or as a solution in a solvent. The process of the invention is preferably carried out without addition of additives.

In a preferred embodiment of the process, no ammonia is added to the solution in which the hydrogenation is carried out. If ammonia is present in dissolved form in the starting materials or in any aqueous solution used or is liberated as by-product in the hydrogenation, this does not interfere. Any ammonia present can be removed by methods known to those skilled in the art, for example by distillation.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also Raney catalyst) which are obtained by leaching (activation) of an alloy of hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated by reduction of the metal oxides in a hydrogen-comprising gas stream at elevated temperature either outside the reactor or in the reactor before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. An exception in the activation is the skeletal catalysts which can be activated by leaching with aqueous base, as described in, for example, EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The active catalyst composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$; for example the catalyst specifically disclosed in this document which has the composition 31.5% by weight of $ZrO_2$, 50% by weight of NiO, 17% by weight of CuO and 1.5% by weight of $MoO_3$. Further suitable catalysts are those described in WO-A-99/44984, which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight based on (a) of a compound based on an alkali metal and/or alkaline earth metal and (d) from 0.001 to 1% by weight based on (a) manganese.

Suspension processes are preferably carried out using Raney catalysts. In the case of Raney catalysts, the active catalyst is produced as "metal sponge" from a binary alloy (nickel, iron, cobalt with aluminum or silicon) by leaching out of one component by means of acid or alkali. Residues of the original alloying component often have a synergistic action.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted with alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air sensitive and pyrophoric and are therefore generally stored and handled under a medium such as water, an organic solvent or a substance which is present in the reaction according to the invention (solvent, starting material, product) or embedded in an organic compound which is solid at room temperature.

According to the invention, preference is given to using a skeletal cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with 1-30% by weight of Al, particularly preferably 2-12% by weight of Al, very particularly preferably 3-6% by weight of Al, 0-10% by weight of Cr, particularly preferably 0.1-7% by weight of Cr, very particularly preferably 0.5-5% by weight of Cr, in particular 1,-3.5% by weight of Cr, 0-10% by weight of Fe, particularly preferably 0.1-3% by weight of Fe, very particularly preferably 0.2-1% by weight of Fe, and/or 0-10% by weight of Ni, particularly preferably 0.1-7% by weight of Ni, very particularly preferably 0.5-5% by weight of Ni, in particular 1-4% by weight of Ni, with the percentages by weight in each case being based on the total weight of the catalyst.

As catalyst in the process of the invention, use can advantageously be made of, for example, a skeletal cobalt catalyst "Raney 2724" from W.R. Grace & Co. This catalyst has the following composition:
Al: 2-6% by weight, Co: $\geq$86% by weight, Fe: 0-1% by weight, Ni: 1-4% by weight, Cr: 1.5-3.5% by weight.

It is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters for the purposes of the invention.

Such catalysts typically comprise nickel together with 1-30% by weight of Al, particularly preferably 2-20% by weight of Al, very particularly preferably 5-14% by weight of Al,
0-10% by weight of Cr, particularly preferably 0.1-7% by weight of Cr, very particularly preferably 1-4% by weight of Cr,
and/or
0-10% by weight of Fe, particularly preferably 0.1-7% by weight of Fe, very particularly preferably 1-4% by weight of Fe,
with the percentages by weight in each case being based on the total weight of the catalyst.

As catalyst in the process of the invention, use can advantageously be made of, for example, a skeletal nickel catalyst A 4000 from Johnson Matthey.

This catalyst has the following composition Al: $\geq$14% by weight, Ni: $\geq$80% by weight, Fe: 1-4% by weight, Cr: 1-4% by weight.

In the case of decreasing activity and/or selectivity of the catalysts, they can be regenerated by methods known to those skilled in the art, as disclosed, for example, in WO 99/33561 and the documents cited therein.

The regeneration of the catalyst can be carried out in the actual reactor (in situ) or on the catalyst which has been removed from the reactor (ex situ). In the case of fixed-bed processes, regeneration is preferably carried out in situ; in the case of suspension processes, part of the catalyst is preferably taken continuously or discontinuously from the reactor, regenerated ex situ and returned.

The temperatures at which the process of the invention is carried out are in the range from 40 to 150° C., preferably from 40 to 120° C.

The pressure prevailing in the hydrogenation is generally in the range from 5 to 300 bar, preferably from 30 to 250 bar, particularly preferably from 50 to 160 bar.

A relationship between the feed rate of the aminoacetonitrile, the yield of ethylenediamine and the proportion of ethylenediamine or the proportions of secondary and tertiary amines in the product has been found. In the process of the invention, the solution in which the aminoacetonitrile is comprised is fed into the reaction vessel at a rate which is not greater than the rate at which the aminoacetonitrile reacts with hydrogen in the hydrogenation. Preference is given to a feed rate of the aminoacetonitrile which is essentially matched to the rate of hydrogenation of aminoacetonitrile by means of hydrogen. Preference is given to feeding only such an amount of aminoacetonitrile which reacts in the reaction with hydrogen into the reaction vessel. This gives a feed rate of the aminoacetonitrile-comprising solution which is related to the concentration of the aminoacetonitrile in the solution used and to the parameters of the reaction kinetics. These are, inter alia, the prevailing temperature, the prevailing pressure and the hydrogen availability, which is also influenced by mixing effects in the reaction. Preference is given to the concentration of aminoacetonitrile in the reaction product mixture being significantly less than 1% by weight, particularly preferably <1000 ppm.

The abovementioned setting of the feed rate of the aminoacetonitrile results in very fast reaction kinetics in order to minimize the formation of by-products, for example secondary and tertiary amines, but also to minimize the decomposition of the aminoacetonitrile used and thus the catalyst consumption.

Even when the catalyst is partially deactivated by addition of, for example, FACH, the desired selectivity can still be achieved by adaptation of the hydrogenation conditions, e.g. increasing the temperature.

In the process of the invention, the solvent can firstly be mixed completely with AAN. The solution, which may, if appropriate, also comprise water and further additives, is subsequently fed into the reaction vessel comprising the catalyst at the required rate. If appropriate, for example in the case of semibatch processes, part of the solution can be initially placed together with the catalyst in the reaction vessel, whereupon the solution is metered in at the required rate. In the case of continuous processes, part of the solvent can also be introduced into the reaction vessel separately from the solution comprising AAN, the solvent and, if appropriate, water. Since AAN is liquid at room temperature, this can also be fed completely separately to the hydrogenation. As an alternative, the introduction of AAN as aqueous solution with separate introduction of the organic solvent is also conceivable.

The process of the invention for preparing ethylenediamine by hydrogenation of aminoacetonitrile can be carried out continuously, semicontinuously or batchwise in the fixed-bed, fluidized-bed or suspension mode in customary reaction vessels which are suitable for catalysis. Reaction vessels in which contacting of the amino nitrile mixture and the catalyst with the gaseous hydrogen under pressure is possible are suitable for carrying out the hydrogenation.

The hydrogenation in the suspension mode can be carried out in a stirred reactor, loop reactor or other backmixed reactor, jet loop reactor, jet nozzle reactor, bubble column reactor or in a cascade of identical or different reactors of these types. In the case of hydrogenation over a fixed-bed catalyst, tube reactors but also shell-end-tube reactors are conceivable.

In the case of a fixed-bed catalyst, the amino nitrile mixture is conveyed through the catalyst bed in an upward or downward direction. However, the suspension mode is preferably used in semibatch and preferably continuous operation.

The hydrogenation of the nitrile groups takes place with liberation of heat which generally has to be removed. Heat removal can be effected by means of built-in heat-exchange surfaces, cooling jackets or external heat exchangers in a circuit around the reactor. The hydrogenation reactor or a hydrogenation reactor cascade can be operated in a single pass. As an alternative, a recycle mode of operation in which part of the output from the reactor is recirculated to the reactor inlet, preferably without prior work-up of the recycle stream, is also possible. This enables optimum dilution of the reaction solution to be achieved. In particular, the recycle stream can be cooled in a simple and inexpensive manner by means of an external heat exchanger and the heat of reaction can thus be removed. The reactor can also be operated adiabatically, with the increase in the temperature of the reaction solution being able to be limited by means of the cooled recycle stream. Since the reactor itself then does not have to be cooled, a simple and inexpensive construction is possible.

After the hydrogenation, the product obtained (EDA) can be purified further if appropriate, for example by separating off the solvent used, water if appropriate and/or the catalyst by methods known to those skilled in the art. Compounds obtained as by-products, for example diethylenetriamine (DETA), or other impurities can likewise be separated off by methods known to those skilled in the art.

In a preferred embodiment, the process of the invention is carried out using tetrahydrofuran as solvent. The temperature in the hydrogenation is preferably from 75 to 125° C., and the pressure is preferably from 50 to 160 bar. The hydrogenation is preferably carried out in the absence of ammonia.

A high space velocity over the catalyst, which is a measure of the activity of the catalyst used, is achieved by means of the process of the invention. The space velocity over the catalyst is preferably from 0.3 to 20 mol of nitrile (corresponds to ~0.2 g to 12 g of AAN/g of cat), preferably from 1 to 10 mol of nitrile (~0.6 g-6 g), per gram of catalyst per hour. The higher the space velocity of the catalyst, the higher the space-time yield of ethylene amines can be.

EXAMPLES

The following examples illustrate the process of the invention. The proportions are given in % by weight unless indicated otherwise. An internal standard, diethylene glycol dimethyl ether (DEGDME), conveyed with the reaction mixture allows quantification of the product by determination of any volatile decomposition products formed. Quantification is effected by means of gas chromatography (GC), with methanol being in each case added to the samples taken in order to homogenize them.

Example 1

Semibatch 3.25 g of a Cr-doped Raney cobalt catalyst and 15 ml of THF are placed in a 270 ml auto-clave. The autoclave is heated to 80° C. and pressurized with hydrogen to a total pressure of 200 bar. A mixture of 13.8 g (0.25 mol) of distilled AAN [12.7g/g(cat)/h], 13.8 g of an internal standard and 4.2 g of water in 106 g of THF is fed in over a period of 20 minutes. The reaction mixture is stirred under reaction conditions for a further 90 minutes. Samples are taken at different times and are homogenized by means of methanol. Immediately after all the AAN solution has been added, AAN can no longer be detected. After an after-hydrogenation time of 90 minutes, the selectivity to EDA is 96% and that to DETA is 2%.

Example 2

Batch 3.25 g of a Cr-doped Raney cobalt catalyst and 13.8 g (0.25 mol) of distilled AAN, 13.8 g of an internal standard and also 4.2 g of water and 121 ml of THF are placed in a 270 ml autoclave. The autoclave is heated to 80° C. and pressurized with hydrogen to a total pressure of 200 bar. The reaction mixture is stirred under reaction conditions for 60 minutes. The reaction mixture is homogenized by means of methanol. AAN can no longer be detected. After a hydrogenation time of 60 minutes, the selectivity to EDA is 74% and that to DETA is 12%.

In a batch hydrogenation, a high AAN concentration is initially present. Accordingly, more AAN is "introduced" than is hydrogenated, which is why the reaction proceeds with lower selectivity.

Example 3

Semibatch 3.25 g of a Cr-doped Raney cobalt catalyst and 15 ml of THF are placed in a 270 ml auto-clave. The autoclave is heated to 80° C. and pressurized with hydrogen to a total pressure of 50 bar. A mixture of 13.8 g (0.25 mol) of distilled AAN (12.7 g/g(cat)/h, ⅓ of the pressure compared to example 1), 13.8 g of an internal standard and 4.2 g of water in 106 g of THF is fed in over a period of 20 minutes. The reaction mixture is stirred under reaction conditions for a further 90 minutes. Samples are taken at different times and are homogenized by means of methanol. After the addition is complete, AAN can no longer be detected. After an after-hydrogenation time of 90 minutes, the selectivity to EDA is 90% and that to DETA is 4%.

Example 4

Semibatch 3.25 g of a Cr-doped Raney cobalt catalyst and 15 ml of THF are placed in a 270 ml auto-clave. The autoclave is heated to 60° C. and pressurized with hydrogen to a total pressure of 50 bar. A mixture of 13.8 g (0.25 mol) of distilled AAN (12.7 g/g(cat)/h, 20° C. lower temperature compared to example 2), 13.8 g of an internal standard and 4.2 g of water in 106 g of THF is fed in over a period of 20 minutes. The reaction mixture is stirred under reaction conditions for a further 90 minutes. Samples are taken at different times and are homogenized by means of methanol. After the addition is complete, 0.8% of AAN can still be detected. After an after-hydrogenation time of 90 minutes, the selectivity to EDA is 82% and that to DETA is 0.4%.

Under the conditions selected, AAN can still be detected at the end of the addition. Thus, rate of addition is faster than the rate of hydrogenation, which results in a lower selectivity.

Example 5

Partial Deactivation by FACH 3.25 g of a Cr-doped Raney cobalt catalyst and 15 ml of THF are placed in a 270 ml auto-clave. The autoclave is heated to 80° C. and pressurized with hydrogen to a total pressure of 50 bar. A mixture of 13.8 g (0.25 mol) of distilled AAN [12.7 g/g(cat)/h], 13.8 g of an internal standard and 4.2 g of water and 69 mg of formaldehyde cyanohydrin in 106 g of THF is fed in over a period of 20 minutes. The reaction mixture is stirred under reaction conditions for a further 90 minutes. Samples are taken at different times and are homogenized by means of methanol. After the addition is complete, 0.7% of AAN can still be detected. After an after-hydrogenation time of 90 minutes, the selectivity to EDA is 84% and that to DETA is 6%.

Owing to the addition of FACH, partial deactivation of the catalyst occurs. AAN is thus introduced too quickly (AAN is detected after the addition is complete), which is reflected in the selectivity.

Example 6

Partial Deactivation by FACH 3.25 g of a Cr-doped Raney cobalt catalyst and 15 ml of THF are placed in a 270 ml auto-clave. The autoclave is heated to 100° C. and pressurized with hydrogen to a total pressure of 50 bar. A mixture of 13.8 g (0.25 mol) of distilled AAN, 13.8 g of an internal standard and 4.2 g of water and 140 mg of formaldehyde cyanohydrin in 106 g of THF is fed in over a period of 20 minutes. The reaction mixture is stirred under reaction conditions for a further minutes. Samples are taken at different times and are homogenized by means of methanol. After the addition is complete, AAN can no longer be detected. After an after-hydrogenation time of 90 minutes, the selectivity to EDA is 92% and that to DETA is 2%.

Adaptation of the conditions (compared to example 5) results in faster hydrogenation and the addition is thus slower than the hydrogenation, which is why the selectivity is increased.

Example 7

Partial Deactivation by FACH 3.25 g of a Cr-doped Raney cobalt catalyst and 15 ml of THF are placed in a 270 ml auto-clave. The autoclave is heated to 100° C. and pressurized with hydrogen to a total pressure of 50 bar. A mixture of 13.8 g (0.25 mol) of distilled AAN, 13.8 g of an internal standard and 4.2 g of water and 1.4 g of formaldehyde cyanohydrin in 106 g of THF is fed in over a period of 20 minutes. The reaction mixture is stirred under reaction conditions for a further 90 minutes. Samples are taken at different times and are home genized by means of methanol. After the addition is complete, 17% of AAN can still be detected. After an after-hydrogenation time of 90 minutes, the selectivity to EDA is 45% and that to DETA is 15%.

Here, it is shown that, as a result of the addition being too fast, relatively large amounts of AAN are left over and only low EDA concentrations can be achieved.

Example 8

Partial Deactivation by FACH 3.25 g of a Cr-doped Raney cobalt catalyst and 15 ml of THF are placed in a 270 ml auto-clave. The autoclave is heated to 120° C. and pressurized with hydrogen to a total pressure of 50 bar. A mixture of 13.8 g (0.25 mol) of distilled AAN, 13.8 g of an internal standard and 4.2 g of water and 1.4 g of formaldehyde cyanohydrin in 106 g of THF is fed in over a period of 20 minutes. The reaction mixture is stirred under reaction conditions for a further 90 minutes. Samples are taken at different times and are homo genized by means of methanol. After the addition is complete, 10% of AAN can still be detected. After an after-hydrogenation time of 90 minutes, the selectivity to EDA is 69% and that to DETA is 8%.

Example 9

Continuous Hydrogenation/Water-free 10 g of Cr-doped Raney cobalt are placed in a 270 ml autoclave provided with baffles and a disk stirrer and 50 standard l (standard liters) of hydrogen are continuously fed in. A 10.5% strength by weight solution of AAN in THF is pumped in continuously at 170-180 bar. Reaction mixture is discharged continuously via an immersed frit. The reaction temperature is maintained at 120° C. The output is depressurized via a regulating valve. The feed rate is increased from 14 g/h of AAN to 27 g/h of AAN. Regular samples are analyzed by means of GC. At no time can AAN be detected in the output. When 27 g/h of AAN are metered in, selectivities to EDA of 97% and to DETA of 2% are obtained.

Example 10

Continuous Hydrogenation 160% by Weight of Water 10 g of Cr-doped Raney cobalt are placed in a 270 ml autoclave provided with baffles and a disk stirrer and 50 standard l of hydrogen are continuously fed in. A mixture of 40 g/h of AAN, 40 g/h of diethylene glycol dimethyl ether (DEGDME) as internal standard and 24 g/h of water in 325 g/h of THF is pumped in continuously at 50 bar for 21 hours. Reaction mixture is discharged continuously via an immersed frit. The reaction temperature is maintained at 120° C. The output is depressurized via a regulating valve. Regular samples are analyzed by means of GC. At no time can AAN be detected in the output. The samples show a constant selectivity to EDA of 96.5% and to DET of 1.5%.

Example 11

Continuous Hydrogenation/30% by Weight of Water 10 g of Cr-doped Raney cobalt are placed in a 270 ml autoclave provided with baffles and a disk stirrer and 50 standard l of hydrogen are continuously fed in. A mixture of 30 g/h of AAN, 9 g/h of water in 255 g/h of THF is pumped in continuously at 50 bar. Reaction mixture is discharged continuously via an immersed frit. The reaction temperature is maintained at 120° C. The output is depressurized via a regulating valve. Regular samples are analyzed by means of GC. At no time can AAN be detected in the output. The samples show a constant selectivity to EDA of >98% and to DET of 1%.

The invention claimed is:

1. A process for preparing ethylenediamine which comprises hydrogenating aminoacetonitrile over a catalyst, wherein the hydrogenation is carried out in a solution comprising aminoacetonitrile, water in a proportion of from 0 to 60% by weight and a solvent and the aminoacetonitrile comprised in the solution is fed into the reaction vessel at a rate which is not greater than the rate at which the aminoacetonitrile reacts with hydrogen in the hydrogenation.

2. The process for preparing ethylenediamine according to claim 1, wherein the solvent is an ether.

3. The process for preparing ethylenediamine according to claim 2, wherein the ether is tetrahydrofuran.

4. The process for preparing ethylenediamine according to claim 1, wherein the aminoacetonitrile of the total fresh feed has a concentration of 5-30% by weight.

5. The process for preparing ethylenediamine according to claim 1, wherein the reaction vessel is a stirred reactor, a loop reactor or another backmixed reactor and the reaction vessel is operated in semibatch or continuous mode.

6. The process for preparing ethylenediamine according to claim 1, wherein the catalyst is a Raney cobalt or Raney nickel catalyst.

7. The process for preparing ethylenediamine according to claim 6, wherein the catalyst is a chromium-doped Raney cobalt or Raney nickel catalyst.

8. The process for preparing ethylenediamine according to claim 1, wherein the hydrogenation is carried out at a temperature of from 40 to 150° C.

9. The process for preparing ethylenediamine according to claim 1, wherein the hydrogenation is carried out at a pressure of from 5 to 300 bar.

10. The process for preparing ethylenediamine according to claim 9, wherein the pressure is from 50 to 160 bar.

11. The process for preparing ethylenediamine according to claim 1, wherein the concentration of the aminoacetonitrile in the reaction product mixture is less than 1% by weight.

12. The process for preparing ethylenediamine according to claim 1, wherein the space velocity over the catalyst is from 0.3 to 20 g of amino nitrile per gram of catalyst per hour.

13. The process for preparing ethylenediamine according to claim 1, wherein the hydrogenation is carried out without addition of ammonia.

14. The process for preparing ethylenediamine according to claim 1, wherein aminoacetonitrile which is largely free of formaldehyde cyanohydrin (FACH) is used or the aminoacetonitrile has been distilled before the hydrogenation.

15. The process for preparing ethylenediamine according to claim 3, wherein the aminoacetonitrile of the total fresh feed has a concentration of 5-30% by weight.

16. The process for preparing ethylenediamine according to claim 15, wherein the reaction vessel is a stirred reactor, a loop reactor or another backmixed reactor and the reaction vessel is operated in semibatch or continuous mode.

17. The process for preparing ethylenediamine according to claim 16, wherein the catalyst is a chromium-doped Raney cobalt or Raney nickel catalyst.

18. The process for preparing ethylenediamine according to claim 17, wherein the hydrogenation is carried out at a temperature of from 75 to 125° C.

19. The process for preparing ethylenediamine according to claim 18, wherein the hydrogenation is carried out at a pressure of from 50 to 160 bar.

* * * * *